United States Patent
Ritter et al.

(10) Patent No.: US 9,855,380 B2
(45) Date of Patent: Jan. 2, 2018

(54) FLUID CONVEYANCE MONITORING SYSTEM IN AN EXTRACORPOREAL BLOOD TREATMENT DEVICE

(71) Applicant: B. BRAUN AVITUM AG, Melsungen (DE)

(72) Inventors: Kai-Uwe Ritter, Rednitzhembach (DE); Christian Schleicher, Dipperz (DE)

(73) Assignee: B. BRAUN AVITUM AG, Melsungen (DE)

( * ) Notice: Subject to any disclaimer, the term of this patent is extended or adjusted under 35 U.S.C. 154(b) by 92 days.

(21) Appl. No.: 15/085,362

(22) Filed: Mar. 30, 2016

(65) Prior Publication Data

US 2016/0296686 A1  Oct. 13, 2016

(30) Foreign Application Priority Data

Apr. 8, 2015  (DE) .................. 10 2015 105 323

(51) Int. Cl.
*A61M 1/26* (2006.01)
*A61M 1/10* (2006.01)
(Continued)

(52) U.S. Cl.
CPC .......... *A61M 1/267* (2014.02); *A61M 1/1086* (2013.01); *A61M 1/367* (2013.01);
(Continued)

(58) Field of Classification Search
None
See application file for complete search history.

(56) References Cited

U.S. PATENT DOCUMENTS 8,882,778 B2   11/2014   Ranft
9,005,153 B2*   4/2015   Kopperschmidt ...... A61M 1/16
                                                              604/6.11
(Continued)

FOREIGN PATENT DOCUMENTS

DE   102006011346   9/2007
DE   10 2008 039 241   5/2009
(Continued)

OTHER PUBLICATIONS

German Search Report for DE 10 2015 105 323.3 dated Oct. 22, 2015, with translation.
(Continued)

*Primary Examiner* — Andre Allen
(74) *Attorney, Agent, or Firm* — RatnerPrestia

(57) ABSTRACT

A method for monitoring conveyance of fluid in a device for extracorporeal blood treatment, whereby fluid is conveyed by a peristaltic pump in a fluid system from a low-pressure side to a high-pressure side in that an elastically deformable fluid line positioned between the low-pressure side and the high-pressure side is deformed between a support surface and at least two squeeze elements of a rotor rotating opposite the support surface in such a way that a conveyance volume section is formed between the squeeze elements, whereby a fluid pressure value in the fluid system is detected for the conveyance volume section that is specific to the conveyance volume section, and whereby the detected conveyance-volume-specific fluid pressure value of a conveyance cycle n is compared with the detected conveyance-volume-specific fluid pressure value of a previous conveyance cycle n−x.

12 Claims, 3 Drawing Sheets

(51) Int. Cl.
  *A61M 1/36* (2006.01)
  *F04B 43/12* (2006.01)
  *F04B 49/08* (2006.01)
  *G01L 13/00* (2006.01)
  *F04B 49/06* (2006.01)

(52) U.S. Cl.
  CPC ........ *A61M 1/3621* (2013.01); *A61M 1/3639* (2013.01); *F04B 43/1253* (2013.01); *F04B 43/1261* (2013.01); *F04B 49/065* (2013.01); *F04B 49/08* (2013.01); *G01L 13/00* (2013.01); *A61M 1/1006* (2014.02); *A61M 1/1039* (2014.02); *A61M 2205/3331* (2013.01); *A61M 2205/3351* (2013.01); *A61M 2205/3355* (2013.01); *A61M 2205/702* (2013.01)

(56) References Cited

U.S. PATENT DOCUMENTS 9,267,500 B2    2/2016    Gronau et al.
2009/0053083 A1    2/2009    Kopperschmidt
2013/0126404 A1    5/2013    Gronau et al.
2013/0204174 A1    8/2013    Olde et al.
2013/0280104 A1    10/2013    Heide et al.
2016/0243296 A1*    8/2016    Schaefer ............. A61M 1/1043
2016/0245271 A1*    8/2016    Schaefer ............. A61M 1/1603

FOREIGN PATENT DOCUMENTS

| | | |
|---|---|---|
| DE | 10 2008 039 022 | 4/2010 |
| DE | 10 2010 033 241 | 2/2012 |
| DE | 10 2011 108 778 | 1/2013 |
| DE | 102012007412 | 10/2013 |
| WO | 2013057109 | 4/2013 |

OTHER PUBLICATIONS

European Search Report with English language translation for EP 16162936.5, dated Sep. 5, 2016, 11 pages.

\* cited by examiner

FLUID CONVEYANCE MONITORING SYSTEM IN AN EXTRACORPOREAL BLOOD TREATMENT DEVICE

CROSS REFERENCE TO RELATED APPLICATIONS

This application claims priority to German application DE 10 2015 105 323.3 filed Apr. 8, 2015, the contents of such application being incorporated by reference herein.

FIELD OF THE INVENTION

The invention concerns a method for monitoring a conveyance of fluid, in particular blood, in a device for extracorporeal blood treatment, in particular a dialysis machine, whereby fluid is conveyed with a peristaltic pump in a fluid system from a low-pressure side to a high-pressure side and an elastically deformable fluid line positioned between the low-pressure side and the high-pressure side is deformed between a support surface, in particular a support surface formed by a housing of a peristaltic pump, and at least two squeeze elements of a rotor rotating opposite the support surface, in such a way that between the squeeze elements, in particular between immediately consecutive or immediately neighbouring squeeze elements, a conveyance volume section is formed, whereby a fluid pressure value in the fluid system is detected for the conveyance volume section which is specific to the conveyance volume section.

BACKGROUND OF THE INVENTION

Known peristaltic pumps in medical devices for extracorporeal blood treatment generally consist of a rotor, a pump housing and a pump line arranged between these as a fluid line and they convey a defined volume of a medium, such as blood or dialysis fluid, from the low-pressure side, normally the arterial side, to the high-pressure side, normally the venous side. The peristaltic pump works by deforming and pinching the elastically deformable fluid line with the squeeze elements. These are pre-tensioned against the fluid line and are moved along the latter on rotation of the rotor, thereby causing elastic deformation of the fluid line in a cross-sectional direction. As a result of this, fluid is pressed out of the fluid line in the direction of conveyance. Replenishing fluid is drawn into the line with low pressure, in particular vacuum, which is created due to the elastic reshaping of the fluid line after deformation by the squeeze elements.

It is known that pre-tensioning of the squeeze elements against the fluid line can be effected with springs, for example. These are designed in such a way that the cross-section of the fluid line can be fully pinched, in other words the cross-section of the fluid line can be fully closed with the squeeze elements. If the pump functions properly, therefore, pressure differences are not transferred from the arterial side to the venous side.

When the conveyance volume is opened, i.e. at the transition of the fluid line cross-section from occlusive to non-occlusive, pulsation occurs on the high-pressure side. This effect is caused by the fact that on the low-pressure side a volume section of the elastic fluid line is pinched and the fluid volume enclosed inside it is conveyed in the direction of the high-pressure side with rotation of the rotor and the shifting of the squeeze point of the fluid line towards the high-pressure side. When the conveyance volume section is pinched, the volume enclosed inside it is under the pressure of the low-pressure side. It is conveyed under this pressure to the high-pressure side, where, by contrast, high pressure prevails. If the conveyance volume section is opened to the high-pressure side as part of the conveyance process, fluid flow occurs from the high-pressure side into the conveyance volume section due to the pressure difference between the high-pressure side and the conveyance volume section. This return flow lasts until pressure balance is established. The result is a momentary interruption of the pressure on the high-pressure side and a pulsation occurs on the high-pressure side.

In the case of a conveyance of blood as the fluid, it can occur during the pressure balance described above and as a result of the fluid line cross-section not being fully closed by the squeeze elements (insufficient sealing of the conveyance volume section) that blood is squeezed through the bottleneck that exists or is formed between the conveyance volume section and the high-pressure side. This normally results in the partial destruction of blood cells, generally referred to as haemolysis. In order to avoid haemolysis, the squeeze elements, the fluid line and the support surface of the peristaltic pump are harmonized in such a way that the cross-section of the fluid line is expanded as quickly as possible when opening the conveyance volume section to the high-pressure side, i.e. the transition between the states occluded and non-occluded is effected as swiftly as possible and also the cross-section is sealed as tightly as possible during conveyance.

It is a disadvantage of known methods for conveying fluid, in particular blood, that wear or failure can occur during the service life of such a peristaltic pump, leading to complete wearing out of the cross-section of the fluid line so that a swift transition from occluded to non-occluded cannot be ensured. Haemolysis can therefore not be reliably ruled out. It is further a disadvantage that a failure of a spring pre-tensioning a squeeze element against the fluid line in conventional methods can only be detected if it happens so completely that the required pressure levels can no longer be established. An undetected failure of the kind described here can potentially cause massive harm to a patient since increased haemolysis can occur.

SUMMARY OF THE INVENTION

Based on the state of the art described above, an object of the present invention is to eliminate the above-mentioned disadvantages, in particular to create a method for the monitoring of the conveyance of fluid and in the broadest sense a method for the conveyance of fluid in which incomplete wear of the cross-section of the fluid line and delayed transition from occluded to non-occluded, in particular wear or error, can be detected reliably and quickly, thereby minimizing the risk of haemolysis.

According to aspects of the invention, this object is achieved with a method for monitoring a conveyance of a fluid in a device for extracorporeal blood treatment or a method for the conveyance of fluid in such a device, whereby fluid is conveyed with a peristaltic pump from a low-pressure side to a high-pressure side in that an elastically deformable fluid line positioned between the low-pressure side and the high-pressure side is deformed between a support surface and at least two squeeze elements of a rotor rotating opposite the support surface in such a way that a conveyance volume section is formed between the squeeze elements, whereby a fluid pressure value is detected in the fluid system for the conveyance volume section that is specific to the conveyance volume section and the detected conveyance-volume-specific fluid pressure value of a conveyance cycle n is compared with the detected conveyance-volume-specific fluid pressure value of a preceding conveyance cycle n−x.

Using the method according to aspects of the invention, it is possible to detect the lack of closure of the cross-section of the fluid line in a particularly advantageous and simple manner. This can occur, for example, as a result of wear or failure of the squeeze elements and/or the elements pretensioned against the fluid line such as springs. What is more, the method according to aspects of the invention can be used to detect wear or ageing of the fluid line, e.g. slackening or bending, especially on the arterial side. Finally, the method can be used to ensure that fluid is conveyed in such a way that an opening of the conveyance volume section when a squeeze element exits the conveyance path, i.e. the transition from occluded to non-occluded, is geared as effectively as possible towards the avoidance of the return flow of fluid from the high-pressure side into the conveyance volume section while at the same time not pressing the squeeze elements too hard against the fluid line so as to avoid excessive wear. It is now possible, in order to avoid haemolysis, to coordinate the squeeze elements and the support surface, also referred to as the pump bed, in such a way that during rotation the transition between the states occluded and non-occluded is effected as quickly as possible. When the state is occluded, it is possible to ensure that the occlusion is as tightly sealed and sustained as possible. On the other hand, it is also possible to ensure that the occlusion is not too hard so as to minimize wear in the pump segment.

The method according to aspects of the invention is preferably realized in relation to a dialysis machine or with a dialysis machine with a peristaltic pump for the conveyance of fluid. The peristaltic pump comprises an elastically deformable fluid line, for example a tube, a support surface supporting the fluid line, in particular formed by a pump housing, and a rotor. The fluid line is positioned between the low-pressure side and the high-pressure side and connects these sides fluidically to one another. Fluid entering the fluid line comes from the low-pressure side, fluid flowing out of the fluid line flows into the high-pressure side. Generally speaking, the low-pressure side is the arterial side and the high-pressure side is the venous side. The rotor comprises at least two squeeze elements. On rotation of the rotor, each squeeze element deforms the fluid line between itself and the support surface. According to this description, the term "conveyance cycle" refers to one complete rotation of the rotor, whereby one rotation is referred to as conveyance cycle n. The rotation of the rotor following conveyance cycle n is referred to as conveyance cycle n+1 and other subsequent rotations are referred to as conveyance cycles n+2, n+3, etc. The term "conveyance cycle n+x" refers to any not further specified conveyance cycle following conveyance cycle n. The rotation of the rotor preceding conveyance cycle n is referred to as conveyance cycle n−1 and other preceding rotations are referred to as conveyance cycles n−2, n−3, etc. The term "conveyance cycle n−x" refers to any of the conveyance cycles preceding conveyance cycle n.

The rotor and the support surface supporting the elastic fluid line are configured and coordinated in such a way that a conveyance path is formed between them. In the area of the conveyance path, the fluid line is deformed between the support surface and a squeeze element transversely to its cross-section and, in the case of proper functioning, squeezed together so as to be essentially tightly sealed. A leading squeeze element does not exit the conveyance path until a trailing squeeze element has entered the conveyance path. In other words, the angle between conveyance path entry and conveyance path exit is larger than the angle between a leading squeeze element and a trailing squeeze element. According to aspects of the invention, therefore, there is always a period or a conveyance path section in which a fluid volume being conveyed between the leading squeeze element and the trailing squeeze element is enclosed between these and, in the case of proper functioning, is sealed. The fluid volume enclosed between two neighbouring squeeze elements in the area of the conveyance path in the present description of the invention is referred to as conveyance volume section.

The rotor comprises at least two squeeze elements. This is the lowest possible number of squeeze elements required to form a defined and in particular a sealed conveyance volume section. The method according to aspects of the invention can also be performed with a rotor comprising more than two squeeze elements, in particular three or four. The relative angular positions of the squeeze elements, i.e. the angles between neighbouring squeeze elements, are preferably 180° in the case of two squeeze elements, 120° in the case of three squeeze elements and 90° in the case of four squeeze elements. The length of the conveyance path is greater in each case. A rotor with two squeeze elements A and B forms two conveyance volume sections, a first conveyance volume section AB between the squeeze elements A and B and a second conveyance volume section BA between the squeeze elements B and A. A rotor with three squeeze elements A, B and C forms three conveyance volume sections, a first conveyance volume section AB between the squeeze elements A and B, a second conveyance volume section BC between the squeeze elements B and C and a third conveyance volume section CA between the squeeze elements C and A. Accordingly, a rotor with four squeeze elements A, B, C and D forms four conveyance volume sections AB, BC, CD and DA.

According to aspects of the invention, the fluid pressure value of a particular conveyance volume section is compared with a reference value allocated to this particular conveyance volume section in the form of the detected conveyance-volume-specific fluid pressure value of a preceding conveyance cycle n−x. Conveyance-volume-specific here means that indirectly or directly consecutive fluid pressure values of a conveyance volume are compared with each other. In reference to the previous paragraph, this means that a fluid pressure value of the conveyance volume section AB of a conveyance cycle n is compared with the recorded fluid pressure value of this conveyance volume section AB of a preceding conveyance cycle n−x. The same applies to other existing conveyance volume sections. The method according to aspects of the invention includes both a monitoring of each conveyance volume section of the pump used in each case as well as a monitoring of individual conveyance volume sections only, i.e. not all conveyance volume sections. It is also possible to say that as part of the monitoring, a fluid pressure value recorded at an earlier stage (during conveyance cycle n−x) for each individual conveyance volume section constitutes a reference value allocated to this conveyance volume section. In the methods according to aspects of the invention, the reference value reflects the normal state, i.e. the operating state at which it can be reliably assumed that fluid is conveyed in the desired manner and the pump is in proper functioning order. At the beginning of the method, this reference value can be recorded with a new pump which does not show any signs of wear. According to the idea on which the invention is based, it is possible to conclude the existence of an error when a particular deviation of the recorded actual fluid pressure values from the reference value occurs. A threshold value can be or have been determined to trigger an error message to this effect. It is therefore also possible to say that the method according to aspects of the invention functions in such a way that actual pressure values are compared with target pressure values, the target pressures values reflecting the proper and desired state of the system and the method.

The squeeze elements can be configured directly on the rotor, in particular forming a single component with the rotor. Alternatively they can be positioned on rotor arms. The squeeze elements can in particular be configured as squeeze rollers or pressure rollers, which advantageously roll off the fluid line non-destructively, or as slide shoes which move over the fluid line in a gliding manner. The squeeze elements can in particular be positioned in a radial direction, i.e. pre-tensioned in a position which squeezes the fluid line. This pre-tension is preferably effected with spring elements.

The invention can especially be used to achieve the following advantages:

reduction or avoidance of haemolysis which is harmful to blood, since defective closing of the cross-section of the fluid line and defective transition from the occluded to the non-occluded state can be detected simply and quickly, a return flow of fluid from the high-pressure area into the conveyance path due to pressure difference can be reduced or avoided in this way, thereby resulting in a reduction or even an avoidance of additional pulsation;

the comparison of two measurements in each case over a time delay allows the precise timing of the spring breakage to be identified;

when comparing two measurements of two cycles, the spring breakage can be identified significantly more quickly than for example with a comparison with a reference value determined by averaging a large number of preceding conveyance cycles.

Preferred embodiments of the invention are claimed in the dependent claims and are explained below.

According to one embodiment, x is a value between 1 and 50, preferably between 5 and 40, particularly preferably between 5 and 30, further preferably between 5 and 20. In particular, the preceding conveyance cycle can be the conveyance cycle n−1, n−2, n−3, n−4, n−5, n−6, n−7, n−8, n−9, n−10 or other even earlier conveyance cycles. The above-specified ranges are to be understood in such a way that x can stand for any whole number in the specified ranges.

An embodiment of the method in which every or virtually every conveyance cycle (i.e. n−1, n−2 or n−3) is monitored functions particularly well in order to detect changes that occur suddenly. The idea underlying this embodiment is that, certain parameters are monitored based on a properly functioning system, and in the event of a sudden change in the parameters being monitored the existence of an error is assumed, for example the sudden occurrence of a spring breakage. This is because when the system is functioning properly, the fluid pressure levels and fluid pressure level progressions of a conveyance volume section do not vary significantly from one conveyance cycle to the next. Patient movement can cause changes in pressure, but these are usually only of very short duration and not periodic. A sudden change in the monitored fluid pressure levels or fluid pressure level progressions is only detected when an error occurs such as incomplete occlusion as the result of spring breakage.

Another embodiment of the method in which conveyance cycles at further spaced intervals of time (for example n−10, n−15, n−20, etc.) are compared with each other is particularly suitable for detecting gradual processes changes, for example as a result of gradually occurring wear in the case of prolonged use.

According to another embodiment of the invention, the registration of the fluid pressure value in the fluid system can consist of registration of the progression of the fluid pressure value. The pressure progression can be subjected to a digital signal analysis. This embodiment of the invention is particularly suitable for detecting smaller errors applicable to the entire conveyance volume section such as slight leakage.

In particular, the power density spectrum of the detected fluid pressure value, in particular the detected progression of the fluid pressure value, of the conveyance cycle n can be compared with the power density spectrum of the reference value. Here, the power density spectrum of each conveyance volume section can be calculated or only that of particular selected conveyance volume sections. Based on the power density spectra of a properly function system, a certain change in the monitored power density spectra indicates the existence of an error. By recording the pressure curves and power density spectra, it is even possible to determine the precise time at which an error occurred. This is because after the error, the power density spectrum of the first conveyance volume section deviates from the power density spectra of preceding periods in which this error did not apply.

In one form of the method, the calculated power density spectra can be compared with an assumed ideal or previously recorded and stored power density spectrum. Any excessive deviations indicate an irregularity. For this purpose, in one form of the invention a threshold value can be or have been defined.

In another form of the method, the power density spectrum of a conveyance volume section can be compared with the power density spectrum of the respective preceding conveyance volume section, i.e. for example the spectrum of conveyance volume section n+1 can be compared with the spectrum of conveyance volume section n, then the spectrum of conveyance volume section n+2 with the spectrum of conveyance volume section n+1, etc.

Furthermore, only the spectra of equivalent conveyance volume sections can be compared with one another. In a peristaltic pump with two squeeze elements A and B and conveyance volume sections AB and BA between these, firstly the spectra of the conveyance volume section AB are always compared with each other, i.e. for example AB(n) with AB(n+1), AB(n+1) with AB(n+2), etc., and secondly the spectra of the conveyance volume sections BA are compared with each other, i.e. for example BA (n) with BA(n+1), BA(n+1) with BA(n+2), etc. Alternatively it is possible to simply compare the power density spectra of successive conveyance volume sections, i.e. AB with BA.

According to one embodiment of the invention, it is possible to determine a correlation function for the conveyance cycle n and the conveyance cycle n−x, in particular the cross-correlation function of the fluid pressure value. A cross-correlation function Rxy(τ) can be used to describe the correlation of two signals x(t) and y(t) given differing time delays t between the two signals. The following can apply, for example $$R_{xy}(\tau) = \lim_{T_F \to \infty} \frac{1}{T_F} \int_{-T_F/2}^{T_F/2} x(t)y(t+\tau)dt$$

In this case, x(t) is the pressure signal and y(t+T) is the pressure signal delayed by T/q, i.e. y(t+T)=x(t+T/q), whereby q is the number of squeeze elements of the rotor. The correlation function R reaches its maximum when the signals are equal. In normal operation it is to be anticipated that signals compared with each other are similar. A threshold value can be or have been determined, in particular after the pump has been started, when it can be safely assumed that the latter is functioning properly. During operation, the value R can be monitored for a change, in particular for a sudden drop. A fixed threshold can also be saved as a limit value.

According to one embodiment of the invention, the fluid pressure value of the venous pressure $p_V$ can be detected. According to another embodiment of the invention, the pre-dialyzer fluid pressure value $p_{BE}$ can be detected. According to a further embodiment of the invention, the fluid pressure value of the arterial pressure $p_A$ can be detected. Any combination of the above-mentioned registrations of pressure values equally lies within the scope of the invention.

In all embodiments of the invention, a threshold value can be or have been defined for the detected fluid pressure value at the exceedance of which an error signal is emitted. It is advantageous for an alarm not to be triggered immediately after a single exceedance of the limit value but for several conveyance volume sections to be observed so as to rule out any potential disruptions that may have been recorded such as patient movements or electromagnetic influence on the sensors.

Finally, a correlation of a detected fluid pressure value or fluid pressure value progression can be determined with a predefined expectation function.

It is also possible to say that the invention concerns a method for operating a blood purification machine with which a blood pump is used to pump blood out of the body for the purpose of blood purification and to pump it back in after blood purification has been carried out. The blood pump can be a pump type which works using rollers. These rollers clamp with a spring force against a tube as a fluid line in the pump and move along the tube, thereby pressing out fluid. The replenishing fluid is drawn into the tube by the sucking effect of the vacuum which is created by the elasticity of the tube. The pressing of the tube by the rollers can be realized with the help of springs. The springs can be designed in such a way that the tube is completely pinched. This pinched tube cushions all pressure signals so that no pressure fluctuations caused by the arterial side are transferred to the venous side. In the same way, pressure fluctuations cannot be transferred from the arterial side to the venous side, since the closed roller runner cushions these pressure fluctuations. With the help of the invention, it is especially possible to detect a broken spring in the roller runner of a blood pump. This error case leads to the tube no longer being capable of being completely pinched and increases the occurrence of haemolysis. The fact that the tube is no longer completely pinched tube firstly means that pressure fluctuations on the arterial side are no longer completely cushioned and are transferred to the venous side. Secondly, a no longer completely pinched tube causes a different pressure fluctuation on roller engagement or roller disengagement. What is more, the power density spectrum would change (a different frequency would become established). These described changes can be used to detect a spring breakage.

BRIEF DESCRIPTION OF THE DRAWINGS

The invention is best understood from the following detailed description when read in connection with the accompanying drawings. Included in the drawings are the following figures.

DETAILED DESCRIPTION OF PREFERRED EMBODIMENTS

Figure 1:
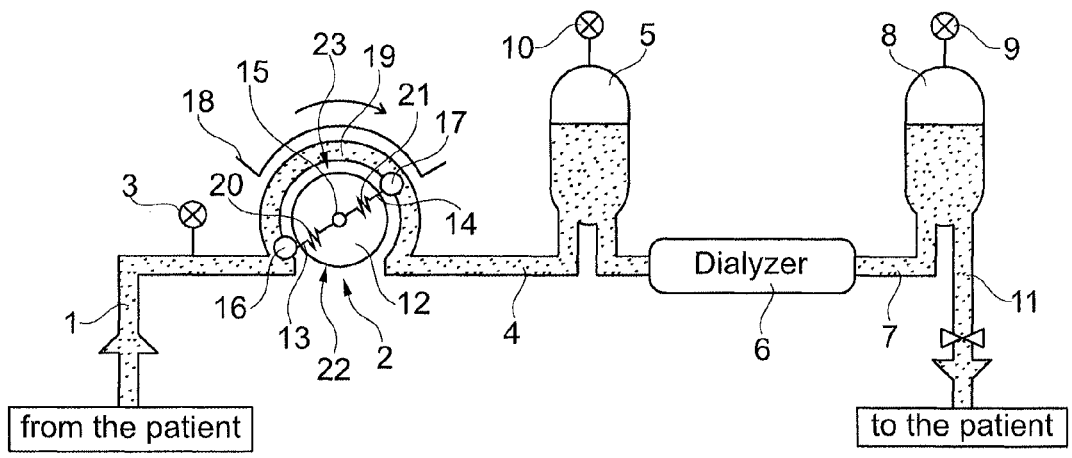
FIG. 1 shows a schematic representation of a section of a device for extracorporeal blood treatment.

FIG. 1 shows by way of an example a section of a device for extracorporeal blood treatment which is operated using the method according to aspects of the invention. The entire extracorporeal blood circuit of the device is essentially shown.

On the low-pressure side this circuit comprises an arterial blood line 1 with which blood is fed from a patient, who is not shown, to a peristaltic pump 2 of the treatment device. Before the peristaltic pump 2, an arterial pressure monitor 3 is provided which measures the pressure before the peristaltic pump 2, i.e., the pressure on the low-pressure or arterial side.

On the high-pressure side, a line 4 feeds as yet untreated blood under high pressure and contaminated with toxins from the peristaltic pump 2 to a droplet chamber 5 and from there to a dialyzer 6. The latter is fed dialysis fluid on the input side (not shown). In the dialyzer 6, blood is treated in familiar fashion with dialysis fluid, e.g. purified. Used dialysis fluid is removed from the dialyzer 6 via a dialysis fluid discharge line, which is not shown, and fed to a disposal or processing unit, which is not shown. Treated blood is fed via a blood discharge line 7 from the dialyzer 6 to a venous droplet chamber 8. On the latter, a venous pressure monitor 9 is provided which detects the venous pressure, i.e. the pressure on the high-pressure side. A pressure monitor 10 is similarly provided at the droplet chamber 5 which can be used to detect the fluid pressure before the dialyzer 6. From the venous droplet chamber 8, treated blood is fed via a venous blood line 11 back to the patient.

The peristaltic pump 2 comprises a rotor 12 with a first rotor arm 13 and a second rotor arm 14. The rotor arms 13, 14 rotate about a common rotor axis 15. The first rotor arm 13 bears on its side facing away from the rotor axis 15 a first squeeze element 16 in the form of a first squeeze roller 16. The second rotor arm 14 bears on its side facing away from the rotor axis 15 a second squeeze element 17 in the form of a second squeeze roller 17. The peristaltic pump 2 further comprises a blood pump housing 18, only schematically indicated in FIG. 1, which forms a support surface for a fluid line 19 in a familiar manner. In the blood pump 18, the elastic fluid line 19 is arranged in such a way that it is deformed between the support surface of the blood pump housing 18 an the squeeze elements 16, 17. The elastic fluid line 19 is connected on the input side, i.e. on the low-pressure side, with the arterial blood line 1 and on the output side, i.e. on the high-pressure side, with the blood line 4. It is deformed by the squeeze elements 16, 17 in such a way that, during normal error-free operation of pump 2 when no wear has occurred, its cross-section is entirely squeezed together and is essentially sealed tightly. The squeeze roller 16 is pre-tensioned in the direction of the fluid line 19 with a spring 20. The squeeze roller 17 is pre-tensioned in the direction of the fluid line 19 with a spring 21. The pre-tension of the springs 20, 21 is selected and set so that the cross-section of the fluid line 19 can be closed to the desired degree.

In the elastic fluid line 19 a first conveyance volume section 22 is formed during operation of the pump 2 by the engagement of the squeeze elements 16, 17 and the consequent squeezing together of the line cross-section between the squeeze element 16 and the squeeze element 17. In this period, the leading squeeze element 16 runs ahead of the trailing squeeze element 17. A second conveyance volume section 23 is formed between the squeeze element 17 and the squeeze element 16. In this period, the leading squeeze element 17 runs ahead of the trailing squeeze element 16.

Figure 2:
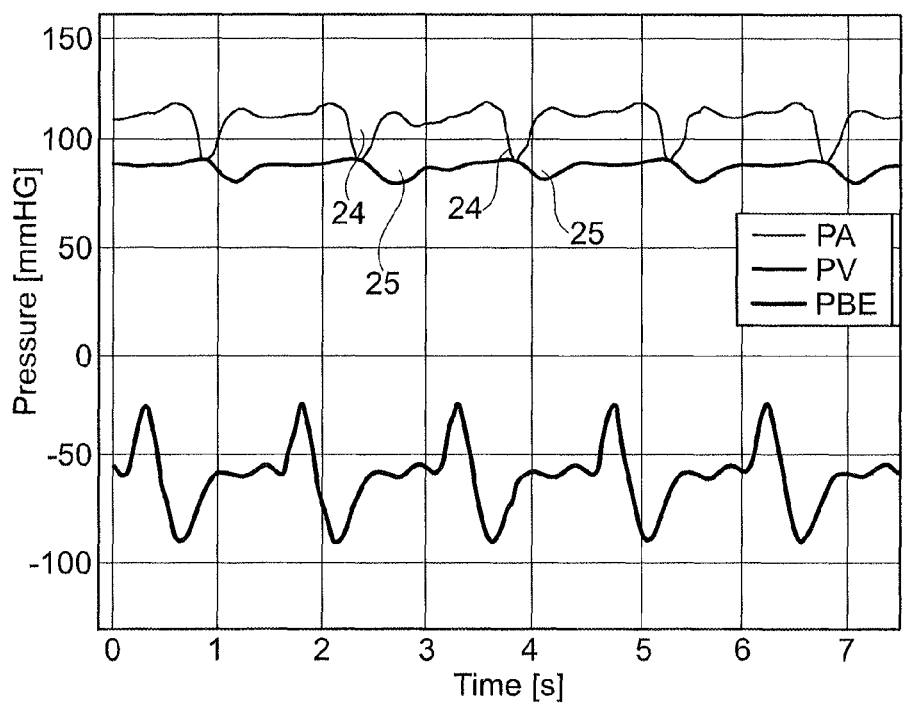
FIG. 2 shows a schematic representation of fluid pressure values under ideal conditions.

FIG. 2 shows fluid pressure values recorded during normal operation of the peristaltic pump 2 of the device described, i.e. without error and wear. The values recorded and shown are the arterial fluid pressure or the arterial fluid pressure progression $p_A$ (detected with the arterial pressure monitor 3), the fluid pressure or fluid pressure progression before the dialyzer 6 $p_{BE}$ (detected with the pressure monitor 10) and the venous fluid pressure or the venous fluid pressure progression $p_V$ (detected with the venous pressure monitor 9). In the normal state shown, both springs 20, 21 are in proper working order and the cross-section of the fluid line 19 is closed in the desired manner by engagement of the squeeze rollers 16, 17. The transition from occluded fluid line 19 to non-occluded fluid line 19 is effected in an optimum manner. In the pressure curve of the venous fluid pressure $p_V$ and in the pressure curve of the fluid pressure $p_{BE}$ before the dialyzer 6 it is possible to identify the squeeze roller disengagements of the blood pump 2 in the form of periodically recurring pressure minimums 24 and 25.

Figure 3:
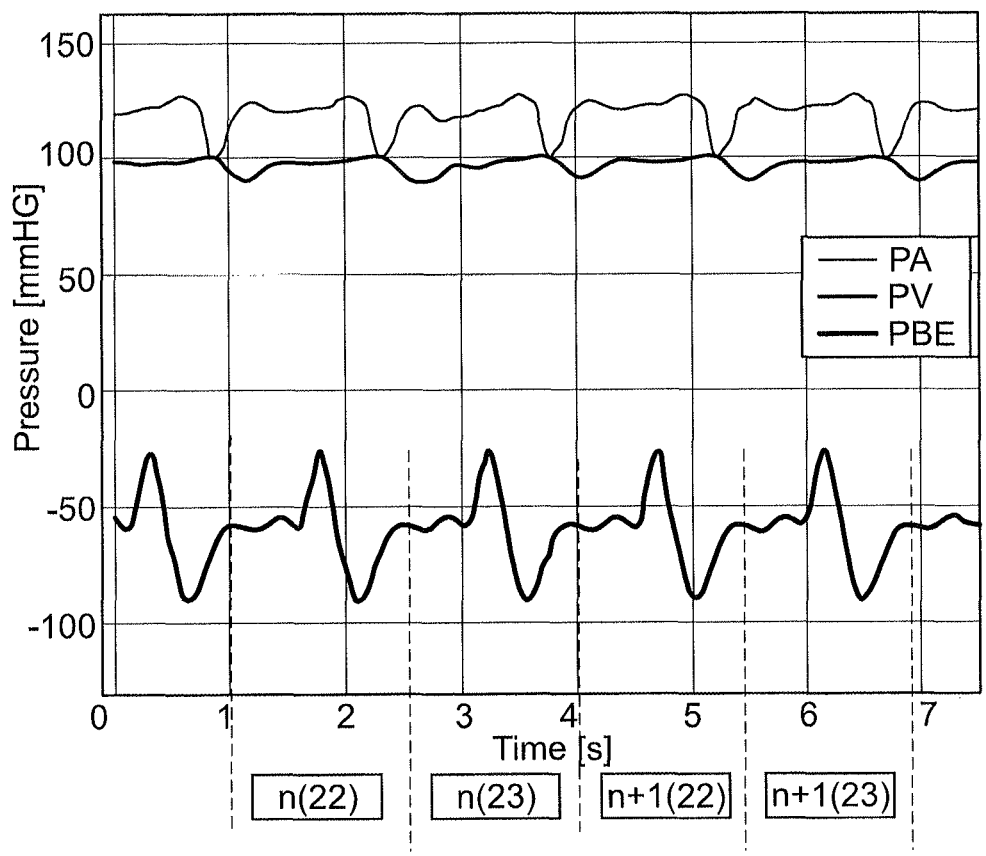
FIG. 3 shows a schematic representation of an analysis of the fluid pressure values of FIG. 2.

According the invention, the fact that these roller disengagements can be identified with a suitable digital signal analysis is put to use. There are various analysis methods here which can be applied according to aspects of the invention. FIG. 3 shows the pressure progressions from FIG. 2 with periodic engagements or periodic value measurements. In one form of the invention, the power density spectrum of every pulse or conveyance volume section is calculated to analyse the values measured, e.g. with fast Fourier transformation of the pressure progressions recorded. In FIG. 3, the first conveyance volume section 22 of a conveyance cycle n is designated n(22). The second conveyance volume section 23 of the conveyance cycle n is designated n(23). The first conveyance volume section 22 of a conveyance cycle n+1 following the conveyance cycle n is designated n+1(22). The second conveyance volume section 23 of the conveyance cycle n+1 is designated n+1(23). FIG. 3 also shows pressure curves during normal operation. It can be recognized that for each conveyance volume section there is a specific signal progression, for which a likewise specific power density spectrum is calculated. If there is no wear and no error, the signal progression relating to the respective conveyance volume section 22 or 23 will essentially remain unchanged.

In the event of a roller disengagement with a broken spring 20 and/or 21, a different pressure fluctuation will be caused than with a flawless spring 20 and/or 21 and there will be a change in the pressure signal recorded, in particular $p_V$ and $p_{BE}$. As a result of this, there will also be a change in the relevant power density spectrum of the conveyance volume section 22 or 23 concerned. By recording the pressure curves and power density spectra, it is even possible to determine the precise time at which a spring breakage occurred. This is because after the spring breakage, the power density spectrum of the first conveyance volume section deviates from the power density spectra of previous periods without a flawless spring.

In one form of the method, the calculated power density spectra can be compared with an assumed ideal or previously recorded and stored power density spectrum. Any excessive deviations indicate an irregularity. A threshold value is generally determined for this purpose. In another form of the method, the power density spectrum of a conveyance volume section can be compared with the power density spectrum of the respective preceding conveyance volume section, i.e. for example the spectrum of conveyance volume section n+1 (22) can be compared with the spectrum of conveyance volume section n(22), then the spectrum of conveyance volume section n+2 (22) with the spectrum of conveyance volume section n+1 (22), etc. In addition, the spectrum of conveyance volume section n+1(23) is compared with the spectrum of conveyance volume section n(23), then the spectrum of conveyance volume section n+2(23) with the spectrum of conveyance volume section n+1(23), etc. In this way, the spectra of the conveyance volume sections generated by the two roller runners are compared with each other. Any excessive deviations indicate an irregularity. A threshold value is generally determined for this purpose. In the case of more than two squeeze elements 16, 17, the method is to be extended in that the power density spectra of the respective conveyance volume sections are compared with the other spectra of the conveyance volume sections. Alternatively it is possible to simply compare the power density spectra of successive conveyance volume sections with each other.

Figure 4:
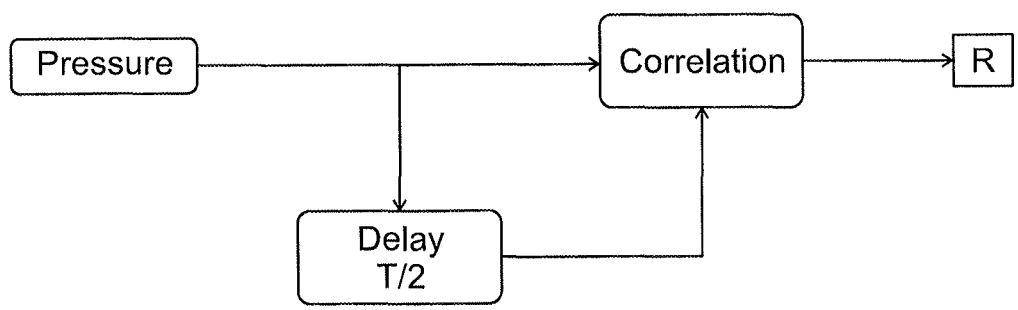
FIG. 4 shows a schematic representation of an analysis of the fluid pressure values based on the correlation of successive pulses.

Another analysis method which can be applied according to aspects of the invention is the analysis of the fluid pressure values with the correlation of successive conveyance volume sections, e.g. with cross-correlation, as shown in FIG. 4. In the signal analysis, the cross-correlation function Rxy(τ) is used to describe the correlation of two signals x(t) and y(t) given differing time delays t between the two signals. The following applies:

$$R_{xy}(\tau) = \lim_{T_F \to \infty} \frac{1}{T_F} \int_{-\frac{T_F}{2}}^{\frac{T_F}{2}} x(t) y(t + \tau) dt$$

In this case, x(t) is the pressure signal and y(t+T) is the pressure signal delayed by T/2 (half the time of a rotor rotation), i.e. y(t+T)=x(t+T/2). The correlation function R reaches its maximum when the signals are equal. In normal operation it is to be anticipated that the signals will be very similar. A threshold value can be fixed shortly after the test when preparing the machine when it can be safely assumed that both springs 20 and 21 and the fluid line 19 are in good condition, i.e. they function in the desired manner. During operation, the value R is then continuously monitored for a change, in particular for a sudden drop. A fixed threshold can also be saved as a limit value.

Figure 5:
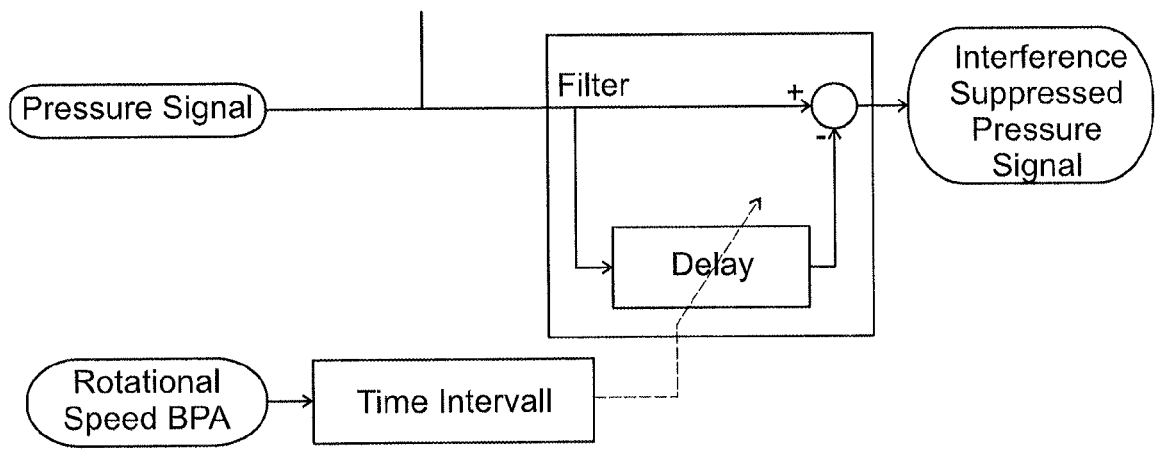
FIG. 5 shows a schematic representation of an analysis of the fluid pressure values based on the comparison of successive pulses.

As part of the method according to aspects of the invention, a third method for the digital signal analysis of the pressure progression can be carried out by comparing the pressure progressions of successive conveyance volume sections. FIG. 5 schematically shows a delay of the pressure progression by a period (rotational speed of the blood pump 2). The optimum delay for a pump 2 with two squeeze elements 16, 17 is half the time (T/2) the blood pump 2 requires for one rotation, i.e. a delay of half a conveyance cycle.

In this type of signal analysis, it is normally to be anticipated that the signals will be very similar and the output result therefore close to zero. A threshold value can be fixed shortly after the test when preparing the machine when it can be safely assumed that both springs 20 and 21 and the tube segment 19 are still in good condition. During operation, the value R is then continuously monitored for a sudden drop. A fixed threshold can also be saved as a limit value.

The invention claimed is:

1. A method for monitoring a conveyance of fluid in a device for extracorporeal blood treatment, the method comprising the steps of:
    conveying fluid in a fluid system with a peristaltic pump from a low-pressure side to a high-pressure side by deforming an elastically deformable fluid line positioned between the low-pressure side and the high-pressure side between a support surface and at least two squeeze elements of a rotor rotating opposite the support surface such that a conveyance volume section is formed between the squeeze elements and conveyed in each of a plurality of conveyance cycles;
    detecting a fluid pressure value in the fluid system for the conveyance volume section in two or more conveyance cycles; and
    comparing the detected conveyance volume fluid pressure value of one conveyance cycle n with the detected conveyance volume specific fluid pressure value of at least one preceding conveyance cycle n–x.

2. The method of claim 1, wherein x is a value between 1 and 50.

3. The method of claim 2, wherein the value is between 5 and 40.

4. The method of claim 3, wherein the value is between 5 and 30.

5. The method of claim 4, wherein the value is between 5 and 20.

6. The method of claim 1, further comprising:
    subjecting pressure progression of the detected fluid pressure value to digital signal analysis.

7. The method of claim 1, further comprising:
    determining a cross-correlation function of the fluid pressure value for the conveyance cycle n and the at least one preceding conveyance cycle n–x.

8. The method of claim 1, wherein the detecting step comprises:
    detecting venous pressure $p_V$.

9. The method of claim 1, wherein the detecting step comprises:
    detecting fluid pressure value $p_{BE}$ before a dialyzer.

10. The method of claim 1, wherein the detecting step comprises:
    detecting arterial pressure $p_A$.

11. The method of claim 1, further comprising:
    emitting an error signal when the detected fluid pressure exceeds a threshold value.

12. The method of claim 1, further comprising:
    determining a correlation with a predefined expectation function.

* * * * *